(12) United States Patent
Smith

(10) Patent No.: US 7,753,860 B1
(45) Date of Patent: Jul. 13, 2010

(54) UTERINE CONTRACTION SENSOR DEVICE

(76) Inventor: Mary-Page Smith, 1460 Upper Bear Creek Rd., Evergreen, CO (US) 80439

( * ) Notice: Subject to any disclaimer, the term of this patent is extended or adjusted under 35 U.S.C. 154(b) by 411 days.

(21) Appl. No.: 11/413,343

(22) Filed: May 1, 2006

(51) Int. Cl.
*A61B 5/103* (2006.01)
*A61B 5/117* (2006.01)

(52) U.S. Cl. ...................... 600/588; 600/587
(58) Field of Classification Search ............... 600/587, 600/588, 591, 304, 594, 595
See application file for complete search history.

(56) References Cited

U.S. PATENT DOCUMENTS

| | | | |
|---|---|---|---|
| 3,521,623 A * | 7/1970 | Markley et. al. ............. 602/13 |
| 4,216,469 A * | 8/1980 | Hirmann et al. ............. 340/666 |
| 4,336,533 A * | 6/1982 | Wettach ...................... 340/666 |
| 4,989,615 A | 2/1991 | Hochberg |
| 5,062,414 A * | 11/1991 | Grim ........................... 602/19 |
| 5,195,536 A | 3/1993 | Silva et al. |
| 5,218,972 A | 6/1993 | Gorsuch et al. |
| D342,571 S | 12/1993 | Givens, Sr. |
| 5,634,476 A | 6/1997 | Orkin et al. |
| 5,871,499 A | 2/1999 | Hahn et al. |
| 5,951,497 A * | 9/1999 | Wallace et al. ............. 600/587 |
| 6,443,906 B1 * | 9/2002 | Ting et al. .................. 600/490 |

* cited by examiner

*Primary Examiner*—Max Hindenburg
*Assistant Examiner*—Helen Nguyen

(57) ABSTRACT

A uterine contraction sensor device for non-invasively monitoring uterine contractions passing through an abdomen includes a base including a top wall, a bottom wall and a perimeter wall extending between the top wall and the bottom wall to define an interior space. The base is positionable on an abdomen. A tube is positioned in the interior space of the base and is coupled to the bottom wall. The tube is filled with a low viscosity fluid. A first end of the tube is closed to inhibit the low viscosity fluid exiting the first end. A second end of the tube extends upwardly from the top wall to be engage by a fetal monitor. A diaphragm is coupled to the tube adjacent the second end of the tube and is engaged by the fetal monitor to transfer vibrations passing through the low viscosity fluid to the fetal monitor.

18 Claims, 2 Drawing Sheets

UTERINE CONTRACTION SENSOR DEVICE

BACKGROUND OF THE INVENTION

1. Field of the Invention

The present invention relates to uterine contraction monitors and more particularly pertains to a new uterine contraction monitor for non-invasively monitoring uterine contractions passing through an abdomen.

2. Description of the Prior Art

The use of uterine contraction monitors is known in the prior art. U.S. Pat. No. 4,989,615 describes a device for being positioned against an abdomen to detect and monitor uterine contractions passing through the abdomen. Another type of uterine contraction monitor is U.S. Pat. No. 5,871,499 for providing pressure to an abdomen in response to uterine contractions to assist in a childbirth process. Another type of uterine contraction monitor is U.S. Pat. No. 5,634,476 for being positioned on an abdomen to measure changes in pressure due to uterine contractions.

While these devices fulfill their respective, particular objectives and requirements, the need remains for a device that has certain improved features to improve contact between the device and an abdomen to provide a greater accuracy in the measurement of uterine contractions passing through the abdomen.

SUMMARY OF THE INVENTION

The present invention meets the needs presented above by generally comprising a base including a top wall, a bottom wall and a perimeter wall extending between the top wall and the bottom wall to define an interior space. The base is positionable on an abdomen. A tube is positioned in the interior space of the base and is coupled to the bottom wall. The tube is filled with a low viscosity fluid. A first end of the tube is closed to inhibit the low viscosity fluid exiting the first end. A second end of the tube extends upwardly from the top wall to permit the second end to be engage by a fetal monitor. A diaphragm is coupled to the tube adjacent the second end of the tube. The diaphragm is engaged by the fetal monitor to transfer vibrations passing through the low viscosity fluid to the fetal monitor.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
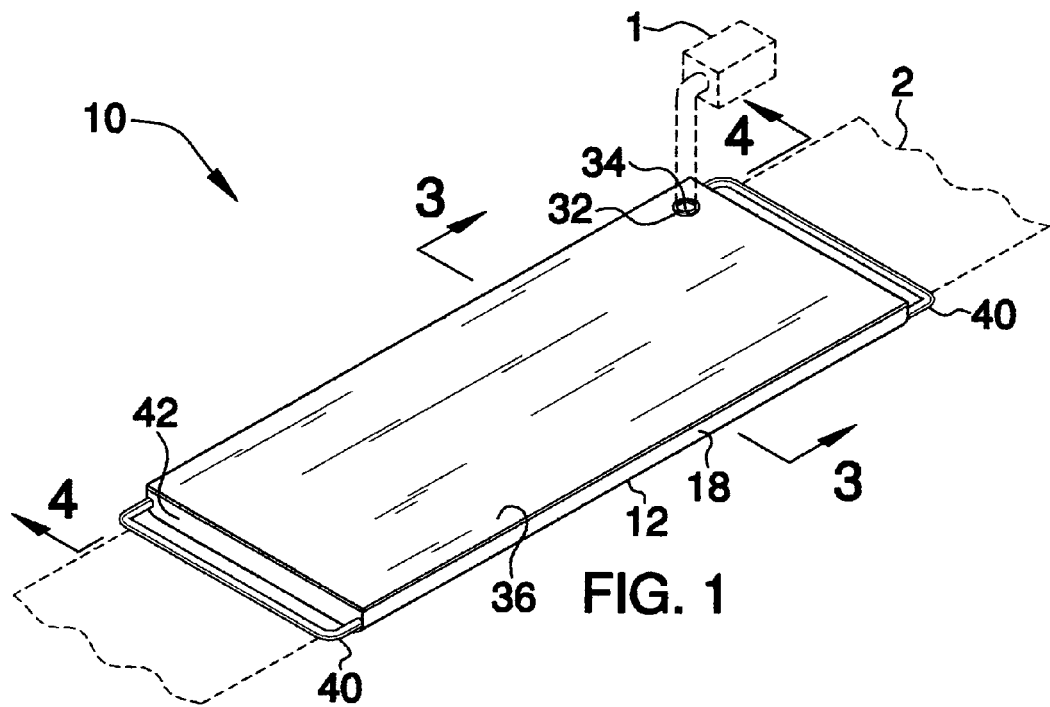
FIG. 1 is a top perspective view of a uterine contraction sensor device according to the present invention.
Figure 2:
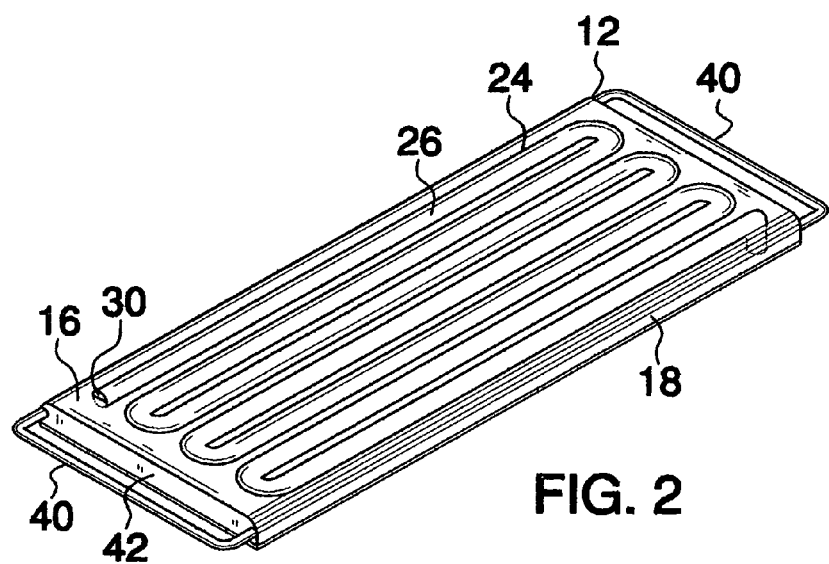
FIG. 2 is a bottom perspective view of the present invention.
Figure 3:
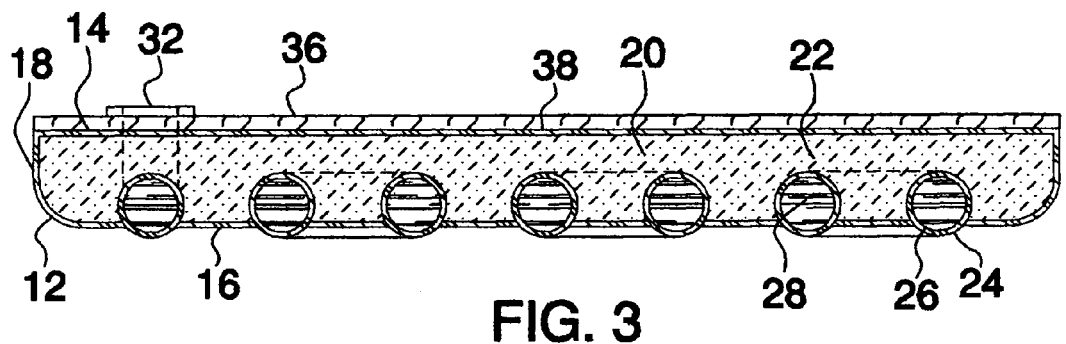
FIG. 3 is a cross-sectional view of the present invention taken along line 3-3 of FIG. 1.
Figure 4:
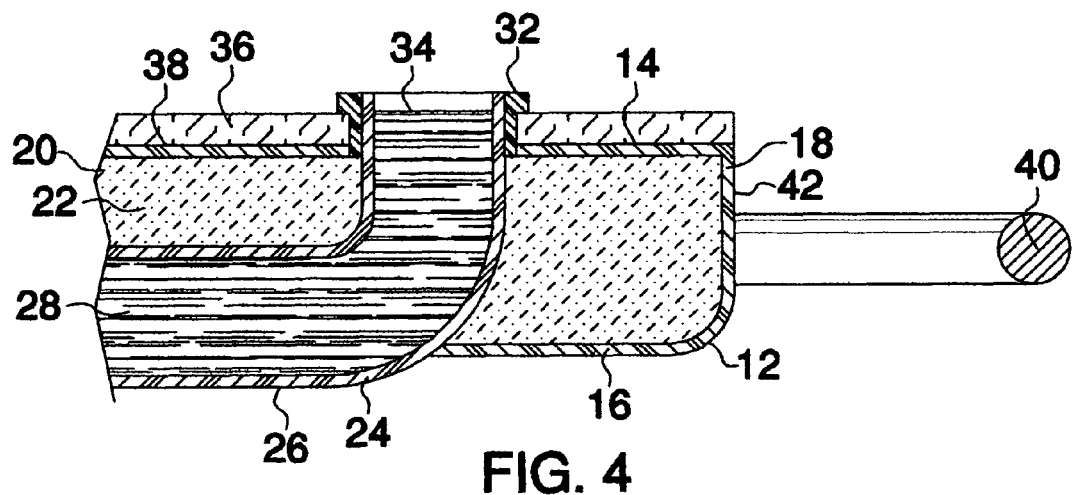
FIG. 4 is a enlarged cross-sectional view of the present invention taken along line 4-4 of FIG. 1.

With reference now to the drawings, and in particular to FIGS. 1 through 4 thereof, a new uterine contraction monitor embodying the principles and concepts of the present invention and generally designated by the reference numeral 10 will be described.

As best illustrated in FIGS. 1 through 4, the uterine contraction sensor device 10 generally comprises a base 12 including a top wall 14, a bottom wall 16 and a perimeter wall 18 extending between the top wall 14 and the bottom wall 16 to define an interior space 20. The base 12 is positionable on an abdomen. The base 12 comprises a flexible material to permit the base 12 to conform to an arcuate contour of the abdomen. A gelatinous material 22 is positioned in the interior space 20 of the base 12. The gelatinous material 22 dampens waves passing through the base 12 from uterine contractions passing through the abdomen.

A tube 24 is positioned in the interior space 20 of the base 12 and is coupled to the bottom wall 16. A lower portion 26 of the tube 24 extends through the bottom wall 16 to permit the tube 24 to directly abut against the abdomen when the base 12 is on the abdomen. The tube 24 comprises a resiliently flexible material to transfer vibrations from contractions passing through the abdomen into the tube 24. The tube 24 is filled with a low viscosity fluid 28 to transfer contractions from the abdomen through the tube 24. A first end 30 of the tube 24 is closed to inhibit the low viscosity fluid 28 exiting the first end 30. A second end 32 of the tube 24 extends upwardly from the top wall 14 to permit the second end 32 to be engage by a fetal monitor 1. The tube 24 is positioned in a serpentine configuration to maximize contact of the tube 24 with the abdomen.

A diaphragm 34 is coupled to the tube 24 adjacent the second end 32 of the tube 24. The diaphragm 34 extends across the second end 32 to inhibit the low viscosity fluid 28 from exiting the second end 32. The diaphragm 34 is engaged by the fetal monitor 1 to transfer vibrations passing through the low viscosity fluid 28 to the fetal monitor 1. A cover 36 is coupled to a top surface 38 of the top wall 14. The second end 32 of the tube 24 extends through the cover 36. Each of a plurality of brackets 40 is coupled to the perimeter wall 18 of the base 12. One of the brackets 40 is coupled to one of a pair of ends 42 of the bracket and positioned opposite the other one of the brackets 40. Each of the brackets 40 is engaged by a strap 2 to permit the base 12 to be strapped across the abdomen.

In use, the back wall of the base 12 is positioned towards the abdomen with the lower portion 26 of the tube 24 extending through the bottom wall 16 of the tube 24 abutting against the abdomen. The brackets 40 are engaged by the strap 2 to allow the base 12 to be secured in over the abdomen. The fetal monitor 1 engages the second end 32 of the tube 24 and the diaphragm 34 to monitor uterine contractions passing through the abdomen to observe the frequency of the uterine contractions.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A uterine contraction sensor device for being connected to a fetal monitor to monitor uterine contractions, said device comprising:
   a base including a top wall, a bottom wall and a perimeter wall extending between said top wall and said bottom wall to define an interior space;
   a tube being positioned in said interior space of said base and being coupled to said bottom wall, said tube filled with a low viscosity liquid, a first end of said tube being closed to inhibit said low viscosity liquid exiting said first end, a second end of said tube extending upwardly from said top wall to permit said second end to be engaged by the fetal monitor, said tube including a lower portion extending through said bottom wall to permit said tube to directly abut against an abdomen when said base is on said abdomen, said tube forming a serpentine pattern extending through said bottom wall; and
   a diaphragm being coupled to said tube adjacent said second end of the tube, said diaphragm being engaged by the fetal monitor to transfer vibrations passing through said low viscosity liquid to the fetal monitor.

2. The device according to claim 1, wherein said base comprises a flexible material to permit said base to conform to an arcuate contour of the abdomen.

3. The device according to claim 1, further comprising a gelatinous material being positioned in said interior space of said base, said gelatinous material dampening waves passing through said base from uterine contractions passing through the abdomen.

4. The device according to claim 1, wherein said tube comprises a resiliently flexible material to transfer vibrations from contractions passing through the abdomen into said tube.

5. The device according to claim 1, wherein said tube is positioned in a serpentine configuration to maximize contact of said tube with the abdomen.

6. The device according to claim 1, wherein said diaphragm extends across said second end to inhibit said low viscosity liquid from exiting said second end.

7. The device according to claim 1, further comprising a cover being coupled to a top surface of said top wall, said second end of said tube extending through said cover.

8. The device according to claim 1, further comprising a plurality of brackets, each of said brackets being coupled to said perimeter wall of said base, each of said brackets being engaged by a strap to permit said base to be strapped across the abdomen.

9. The device according to claim 8, wherein one of said brackets is coupled to one of a pair of ends of said base and positioned opposite the other one of said brackets.

10. A uterine contraction sensor device for being connected to a fetal monitor to monitor uterine contractions, said device comprising:
    a base including a top wall, a bottom wall and a perimeter wall extending between said top wall and said bottom wall to define an interior space, said base being positionable on an abdomen, said base comprising a flexible material to permit said base to conform to an arcuate contour of the abdomen;
    a gelatinous material being positioned in said interior space of said base, said gelatinous material dampening waves passing through said base from uterine contractions passing through the abdomen;
    a tube positioned in said interior space of said base and being coupled to said bottom wall, a lower portion of said tube extending through said bottom wall to permit said tube to directly abut against the abdomen when said base is on said abdomen, said tube comprising a resiliently flexible material to transfer vibrations from contractions passing through the abdomen into said tube, said tube being filled with a low viscosity liquid, a first end of said tube being closed to inhibit said low viscosity liquid exiting said first end, a second end of said tube extending upwardly from said top wall to permit said second end to be engaged by the fetal monitor, said tube being positioned in a serpentine configuration to maximize contact of said tube with the abdomen;
    a diaphragm being coupled to said tube adjacent said second end of said tube, said diaphragm inhibiting said low viscosity liquid from exiting said second end, said diaphragm being engaged by the fetal monitor to transfer vibrations passing through said low viscosity liquid to the fetal monitor;
    a cover being coupled to a top surface of said top wall, said second end of said tube extending through said cover; and
    a plurality of brackets, each of said brackets being coupled to said perimeter wall of said base, one of said brackets being coupled to one of a pair of ends of said base and positioned opposite the other one of said brackets, each of said brackets being engaged by a strap to permit said base to be strapped across the abdomen.

11. A uterine contraction sensor system comprising:
    a fetal monitor to monitor uterine contractions;
    a base including a top wall, a bottom wall and a perimeter wall extending between said top wall and said bottom wall to define an interior space, said base being positionable on an abdomen;
    a tube being positioned in said interior space of said base and being coupled to said bottom wall, said tube being filled with a low viscosity liquid, a first end of said tube being closed to inhibit said low viscosity liquid exiting said first end, a second end of said tube engaging the fetal monitor, said tube including a lower portion extending through said bottom wall to permit said tube to directly abut against the abdomen when said base is on said abdomen, said tube forming a serpentine pattern extending through said bottom wall; and
    a diaphragm being coupled to said tube adjacent said second end of said tube, said diaphragm being engaged by the fetal monitor to transfer vibrations passing through said low viscosity liquid to the fetal monitor.

12. The system according to claim 11, wherein said base comprises a flexible material to permit said base to conform to an arcuate contour of the abdomen.

13. The system according to claim 11, further comprising a gelatinous material being positioned in said interior space of said base, said gelatinous material dampening waves passing through said base from uterine contractions passing through the abdomen.

14. The system according to claim 11, wherein said tube comprises a resiliently flexible material to transfer vibrations from contractions passing through the abdomen into said tube.

15. The system according to claim 11, wherein said tube is positioned in a serpentine configuration to maximize contact of said tube with the abdomen.

16. The system according to claim 11, wherein said diaphragm extends across said second end to inhibit said low viscosity liquid from exiting said second end.

17. The system according to claim 11, further comprising a plurality of brackets, each of said brackets being coupled to said perimeter wall of said base, each of said brackets being engaged by a strap to permit said base to be strapped across the abdomen.

18. The system according to claim 17, wherein one of said brackets is coupled to one of a pair of ends of said base and positioned opposite the other one of said brackets.

* * * * *